United States Patent [19]

Rise

[11] Patent Number: 5,792,186
[45] Date of Patent: Aug. 11, 1998

[54] METHOD AND APPARATUS FOR TREATING NEURODEGENERATIVE DISORDERS BY ELECTRICAL BRAIN STIMULATION

[75] Inventor: Mark T. Rise, Monticello, Minn.

[73] Assignee: Medtronic, Inc., Minneapolis, Minn.

[21] Appl. No.: 847,654

[22] Filed: Apr. 30, 1997

Related U.S. Application Data

[62] Division of Ser. No. 637,440, Apr. 25, 1996, Pat. No. 5,683,422.

[51] Int. Cl.$^6$ .................................................. A61N 1/02
[52] U.S. Cl. .................................................. 607/2
[58] Field of Search .................................. 607/2, 45, 46

[56] References Cited

U.S. PATENT DOCUMENTS

| | | |
|---|---|---|
| 3,850,161 | 11/1974 | Liss ................................ 607/45 |
| 3,918,461 | 11/1975 | Cooper ........................... 607/45 |
| 3,920,024 | 11/1975 | Bowers . |
| 3,957,036 | 5/1976 | Normann . |
| 3,993,046 | 11/1976 | Fernandez . |
| 4,524,774 | 6/1985 | Hildebrandt . |
| 4,570,640 | 2/1986 | Barsa . |
| 4,580,569 | 4/1986 | Petrofsky . |
| 4,690,145 | 9/1987 | King-Smith . |
| 4,702,254 | 10/1987 | Zabara . |
| 4,750,499 | 6/1988 | Hoffer . |
| 4,838,272 | 6/1989 | Liebar . |
| 4,867,164 | 9/1989 | Zabara ............................ 607/45 |
| 4,909,255 | 3/1990 | Farin . |
| 5,002,053 | 3/1991 | Garcia-Rill et al. . |
| 5,025,807 | 6/1991 | Zabara . |
| 5,031,618 | 7/1991 | Mullett . |
| 5,058,584 | 10/1991 | Bourgeois . |
| 5,167,229 | 12/1992 | Peckham . |
| 5,293,879 | 3/1994 | Vonk . |
| 5,314,458 | 5/1994 | Najafi . |
| 5,330,505 | 7/1994 | Cohen . |
| 5,370,672 | 12/1994 | Fowler et al. . |
| 5,540,734 | 7/1996 | Zabara ............................ 607/45 |

FOREIGN PATENT DOCUMENTS

| | | |
|---|---|---|
| 0236513 | 9/1987 | European Pat. Off. . |
| WO 95/19804 | 7/1995 | WIPO . |

OTHER PUBLICATIONS

Crichton, "The Terminal Man," *First Ballantine Books Edition* (Jan. 1988). pp. 16–27 (Copyright 1972).

Durand, "Electrical stimulation can inhibit synchronized neuronal activity," *Brain Research*, 382 pp. 139–144 (1986).

Durand et al., "Desynchronization of epileptiform activity by extracellular current pulses in rat hippocampal slices," *J. Of Physiology*, 480.3, pp. 527–537 (1994).

Durand et al., "Control of Abnormal Electrical Activity with Applied Electrical Fields," IEEE Engineering In Medicine & Biology Society 10th Annual International Conference, pp. 942–943 (1988).

Osorio et al., "A Method for Accurate Automated Real–Time Seizure Detection," *Epilepsia*, vol. 36, Supplement 4 (1995).

Qu et al., "A seizure warning system for long–term epilepsy monitoring," *Neurology*, 45: pp. 2250–2254 (1995).

Schiff et al., "Controlling chaos in the brain," *Nature* vol. 370, pp. 615–620 (1994).

Velasco et al., "Electrical Stimulation of the Centromedian Thalamic Nucleus in Control of Seizures: Long–Term Studies", *Epilepsia* 36(1) pp. 63–71 (1993).

*Primary Examiner*—William E. Kamm
*Assistant Examiner*—George R. Evanisko
*Attorney, Agent, or Firm*—Banner & Witcoff Ltd

[57] ABSTRACT

Techniques for stimulating the brain to reduce the effects of neurodegenerative disorders by an implantable signal generator and electrode. A sensor is used to detect the symptoms resulting from the disorder. A microprocessor algorithm analyzes the output from the sensor in order to regulate the stimulation delivered to the brain.

18 Claims, 7 Drawing Sheets

METHOD AND APPARATUS FOR TREATING NEURODEGENERATIVE DISORDERS BY ELECTRICAL BRAIN STIMULATION

This is a divisional of application Ser. No. 08/637,440, filed Apr. 25, 1996 now U.S. Pat. No. 5,683,422.

BACKGROUND OF THE INVENTION

1. Field of the Invention

This invention relates to brain stimulation techniques, and more particularly relates to such techniques for treating neurodegenerative disorders.

2. Description of Related Art

Neuroscientists have recognized and continue to explore excitotoxicity, a phenomenon referring to excessive excitation of nerve cells leading to degeneration of the nervous system. This phenomena has been used to explain cell loss after stroke or some other hypoxic event. The research has focused on nerve cells that have glutamate neurotransmitter receptors especially susceptible to the sustained insult. Hyperexcitation of these nerve cells is fundamental to the mechanism (Rothman, S. M., Olney, J. W. (1987) *Trends Neurosci*. 10, 299-302). Researchers have also used excitotoxicity to explain the observed cell loss in the CA1 region of the Horn of Ammon in the dentate gyrus of hippocampus in patients and animal subjects that have suffered from seizure activity. Seizures can be viewed as a form of abnormal over excitation of the nerve cells in this region.

Typically, neuroscientists have focused on nerve cells that use the transmitter substance glutamate to communicate with target nerve cells; however, other excitatory amino acids (EAA) are included. When nerve cells are abnormally active, experiencing a lot of action potentials, they are believed to release excessive amounts of glutamate or other EAA at their synaptic terminals. The presence of excessive amounts of glutamate leads to toxic effects on the secondary nerve cells targeted by the hyperactive ones. These toxic effects are believed to be mediated by an accumulation of calcium.

Benabid et al. (*The Lancet*, Vol 337:Feb. 16, 1991, pp 403-406) has shown that stimulation of the Vim nucleus of the Thalamus will block tremor. In this instance, stimulation at frequencies around 100 to 185 pulses per second accomplishes the same physiological response as a lesion of this region. Thus, it appears that stimulation inhibits the output of these cells. Benabid's research team has extended this work to stimulation of the subthalamus ("Vim and STN Stimulation in Parkinson's disease", *Movement Disorders, Vol. 9, Supplement* 1 (1994); "Effect on Parkinsonian signs and symptoms of bilateral subthalamic nucleus stimulation", *The Lancet*, Vol 345, Jan. 14, 1995.

Parkinson's disease is the result of degeneration of the substantia nigra pars compacta. The cells of subthalamus have been shown to use glutamate as the neurotransmitter effecting communication with their target cells of the basal ganglia. The state of hyperexcitation that exists in Parkinson's disease will cause an excessive release of glutamate. This, in theory, will lead to further degeneration via the mechanism described above.

Alim Benabid has proposed a method of arresting degeneration of the substantia nigra by high frequency electrical pulsing of the subthalamic nucleus to block stimulation of the subthalamic nucleus, thereby inhibiting excessive release of glutamate at the terminal ends of the axons projecting from the subthalamic nucleus to the substantia nigra.

SUMMARY OF THE INVENTION

A preferred form of the invention can treat a neurodegenerative disorder, such as Parkinson's disease, by means of an implantable signal generator and an implantable electrode having a proximal end coupled to the signal generator and having a stimulation portion for therapeutically stimulating the brain. The electrode is implanted in the brain so that the stimulation portion lies adjacent to a predetermined site in the basal ganglia or thalamus of the brain. The signal generator is operated to pulse the electrode at a predetermined rate and amplitude. By using the foregoing method, the effects of the neurodegenerative disorders are reduced. According to one embodiment of the invention, the stimulation can increase excitement of the thalamus or decrease inhibition of the thalamus.

Another form of the invention uses a sensor in combination with the signal generator and the stimulating electrode to treat a neurodegenerative disorder. In this form of the invention, the sensor generates a sensor signal relating to the excitement of the subthalamus region of the brain. Control means responsive to the sensor signal regulate the signal generator so that the stimulation is increased in response to an increase in the excitation and is decreased in response to a decrease in the excitation.

By using the foregoing techniques, as soon as the diagnosis of a degenerative disorder is made, neurodegeneration can be controlled to a degree unattainable by prior art methods or apparatus.

BRIEF DESCRIPTION OF THE DRAWINGS

These and other advantages and features of the invention will become apparent upon reading the following detailed description and referring to the accompanying drawings in which like numbers refer to like parts throughout and in which.

DESCRIPTION OF THE PREFERRED EMBODIMENTS

Figure 1:
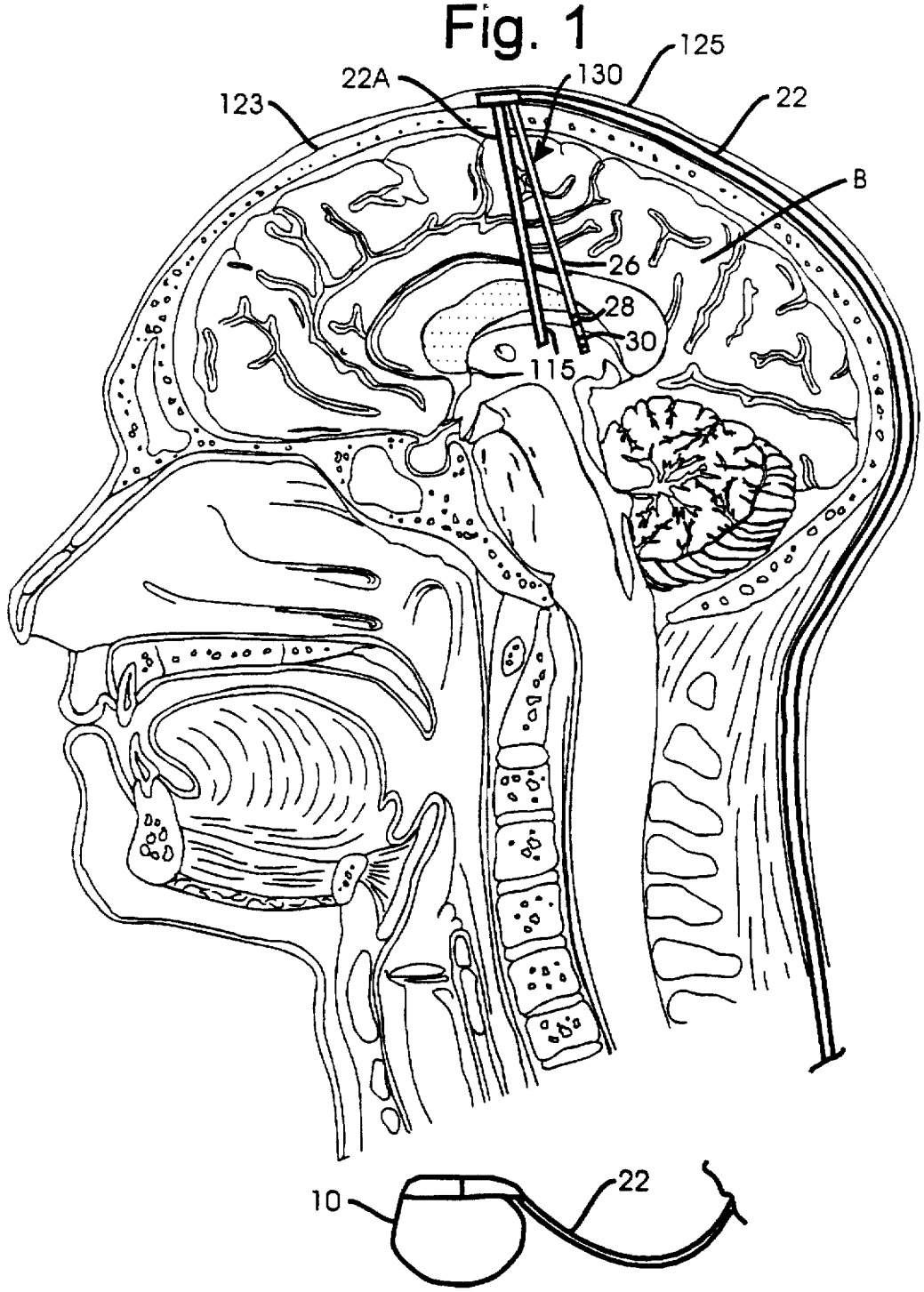
FIG. 1 is a diagrammatic illustration of a stimulation electrode and sensing electrode implanted in a brain according to a preferred embodiment of the present invention and a signal generator coupled to the electrode.

Referring to FIG. 1, a system or device 10 made in accordance with the preferred embodiment may be implanted below the skin of a patient. A lead 22A is positioned to stimulate a specific site in a brain (B). Device 10 may take the form of a modified signal generator Model 7424 manufactured by Medtronic, Inc. under the trademark Itrel II which is incorporated by reference. Lead 22A may take the form of any of the leads sold with the Model 7424 for stimulating the brain. Lead 22A is coupled to device 10 by a conventional cable 22.

The distal end of lead 22A preferably terminates in four stimulation electrodes generally designated 115, although other numbers of electrodes, such as two or six, also are suitable for some applications. Lead 22A is implanted into a portion of the basal ganglia or thalamus of the brain by conventional stereotactic surgical techniques. Each of the four electrodes is individually connected to device 10 through lead 22A and cable 22. Lead 22A is surgically implanted through a hole in the skull 123, and cable 22 is implanted between the skull and the scalp 125 as shown in FIG. 1. Cable 22 is joined to implanted device 10 in the manner shown. Implanted in the brain is a sensor 130 comprising a sensing lead 26 having two sensing electrodes 28 and 30 located in the subthalamic region, substantia nigra or other brain region whose electrical activity reflects the activity of the degenerating neurons, i.e., the neurons exhibiting hyperexcitation. Alternatively, electrodes 28 and 30 could be carried by lead 22A. Electrodes 28 and 30 are connected to an analog to digital converter 206 (FIG. 2) by conductors 134 and 135 which are located within cable 22. The potentials sensed by electrodes 28 and 30 indicate the electrical activity in the subthalamic nucleus and consequently the substantia nigri. Electrodes 28 and 30 transmit a signal related to the excitation of the portion of the brain exhibiting hyperexcitation.

Figure 2:
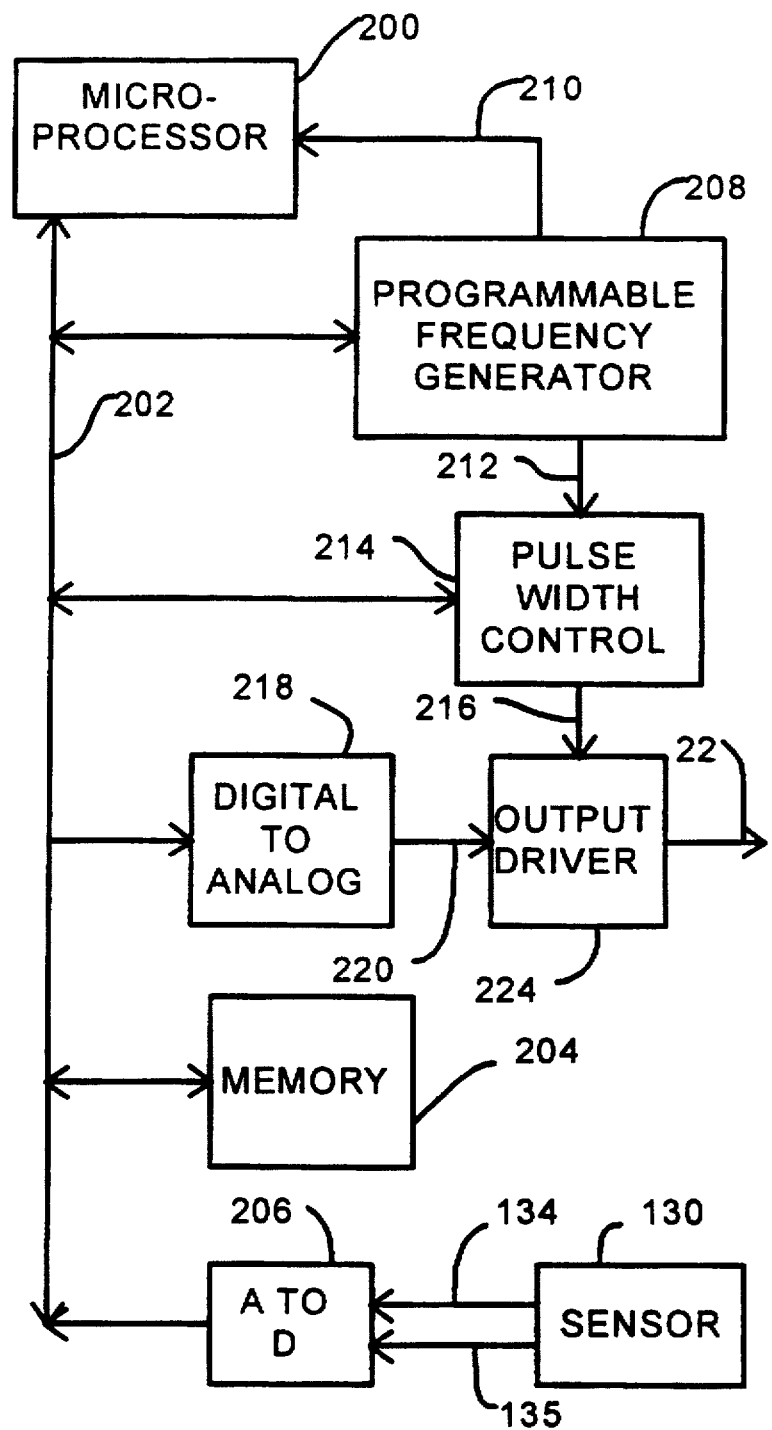
FIG. 2 is a schematic block diagram of a microprocessor and related circuitry used in the preferred embodiment of the invention.

If no sensor is used (i.e., if stimulation is by an open loop technique), device 10 may be a modified signal generator manufactured by Medtronic, Inc. under the trademark Itrel II. If sensor 130 is used, the Itrel II generator is further modified as shown in FIG. 2 to provide a closed loop feedback system.

The output of sensor 130 is coupled by cable 22, comprising conductors 134 and 135, to the input of an analog to digital converter 206. Alternatively, the output of an external sensor would communicate with the implanted pulse generator through a telemetry downlink. The output of the analog to digital converter 206 is connected to a microprocessor 200 through a peripheral bus 202 including address, data and control lines. Microprocessor 200 processes the sensor data in different ways depending on the type of transducer in use. When the signal on sensor 130 exceeds a level programmed by the clinician and stored in a memory 204, increasing amounts of stimulation will be applied through an output driver 224.

The stimulus pulse frequency is controlled by programming a value to a programmable frequency generator 208 using bus 202. The programmable frequency generator provides an interrupt signal to microprocessor 200 through an interrupt line 210 when each stimulus pulse is to be generated. The frequency generator may be implemented by model CDP1878 sold by Harris Corporation.

The amplitude for each stimulus pulse is programmed to a digital to analog converter 218 using bus 202. The analog output is conveyed through a conductor 220 to an output driver circuit 224 to control stimulus amplitude.

Microprocessor 200 also programs a pulse width control module 214 using bus 202. The pulse width control provides an enabling pulse of duration equal to the pulse width via a conductor 216. Pulses with the selected characteristics are then delivered from device 10 through cable 22 and lead 22A to the basal ganglia, thalamus or other region of the brain.

Alternatively, lead 26 could be an electrochemical sensor that measures the amount of glutamate present in the nigra. Such a sensor may take the form of a transducer consisting of an electrode with an ion selective coating applied which is capable of directly transducing the amount of a particular transmitter substance or its breakdown by-products found in the interstitial space of a region of the brain, such as the subthalamic nucleus or the substantia nigra. The level of the interstitial transmitter substance is an indicator of the relative activity of the brain region. An example of this type of transducer is described in the paper "Multichannel semiconductor-based electrodes for in vivo electrochemical and electrophysiological studies in rat CNS" by Craig G. van Horne, Spencer Bement, Barry J. Hoffer, and Greg A. Gerhardt, published in *Neuroscience Letters*, 120 (1990) 249–252. Such a sensor transmits a signal related to the excitation of a portion of the brain exhibiting hyperexcitation.

Microprocessor 200 executes an algorithm shown in FIGS. 3–7 in order to provide stimulation with closed loop feedback control. At the time the stimulation device 10 is implanted, the clinician programs certain key parameters into the memory of the implanted device via telemetry. These parameters may be updated subsequently as needed. Step 400 in FIG. 3 indicates the process of first choosing whether the neural activity at the stimulation site is to be blocked or facilitated (step 400(1)), and whether the sensor location is one for which an increase in the neural activity at that location is equivalent to an increase in neural activity at the stimulation target or vice versa (step 400(2)). Next the clinician must program the range of values for pulse width (step 400(3)), amplitude (step 400(4)) and frequency (step 400(5)) which device 10 may use to optimize the therapy. The clinician may also choose the order in which the parameter changes are made (step 400(6)). Alternatively, the clinician may elect to use default values.

Figure 3:
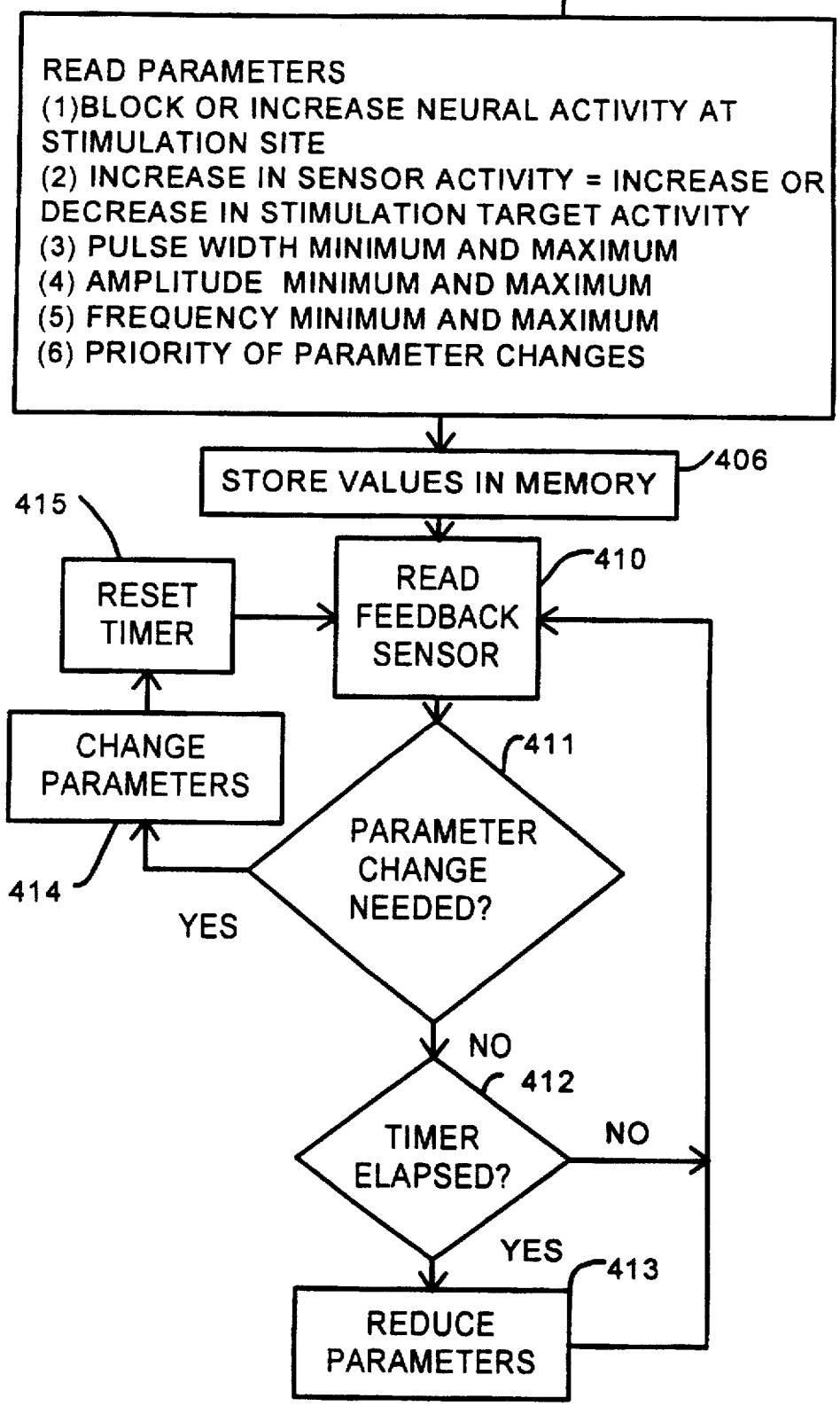
FIGS. 3-7 are flow charts illustrating a preferred form of a microprocessor program for generating stimulation pulses to be administered to the brain.

The algorithm for selecting parameters is different depending on whether the clinician has chosen to block the neural activity at the stimulation target or facilitate the neural activity. FIG. 3 details steps of the algorithm to make parameter changes.

Figure 4:
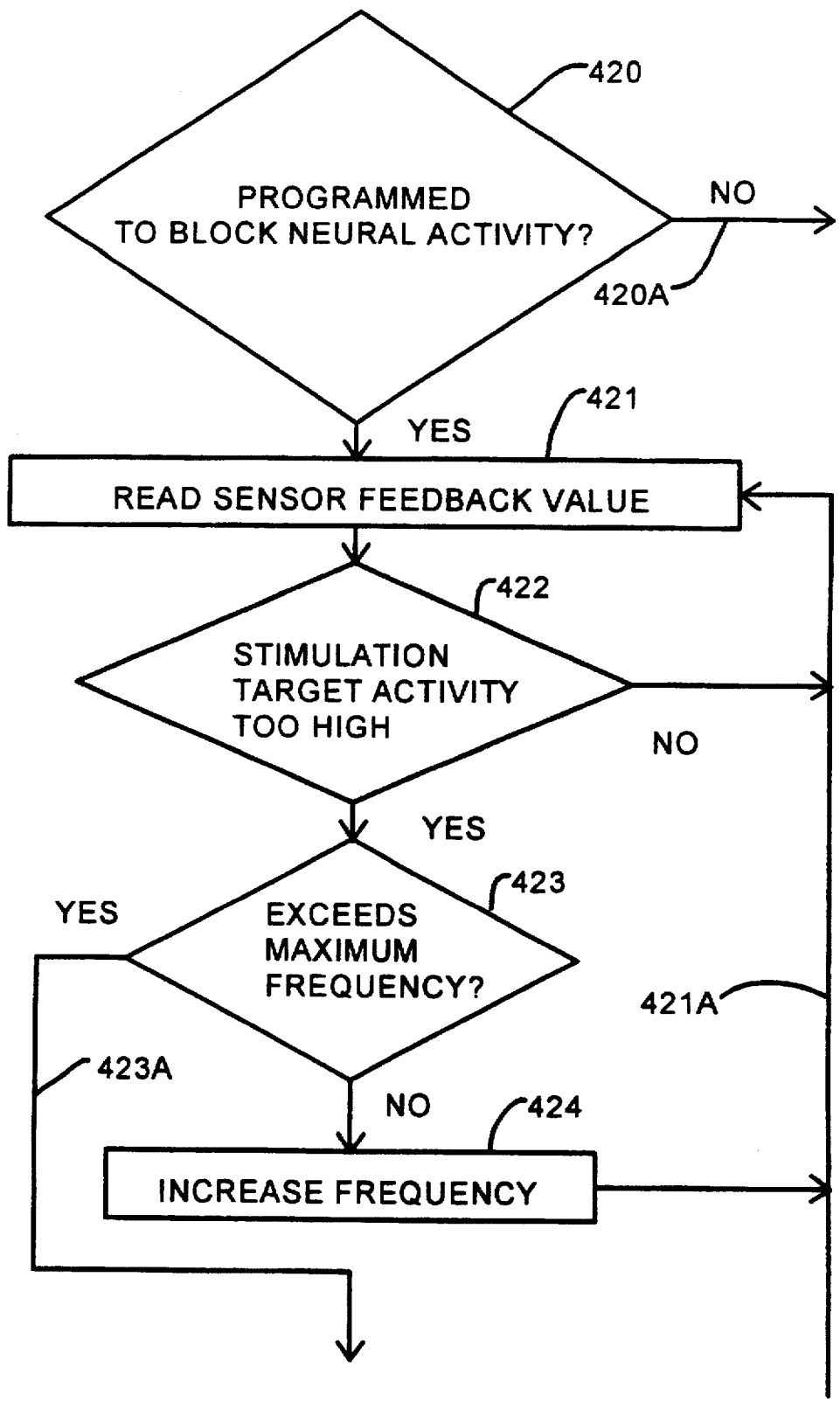
Figure 5:
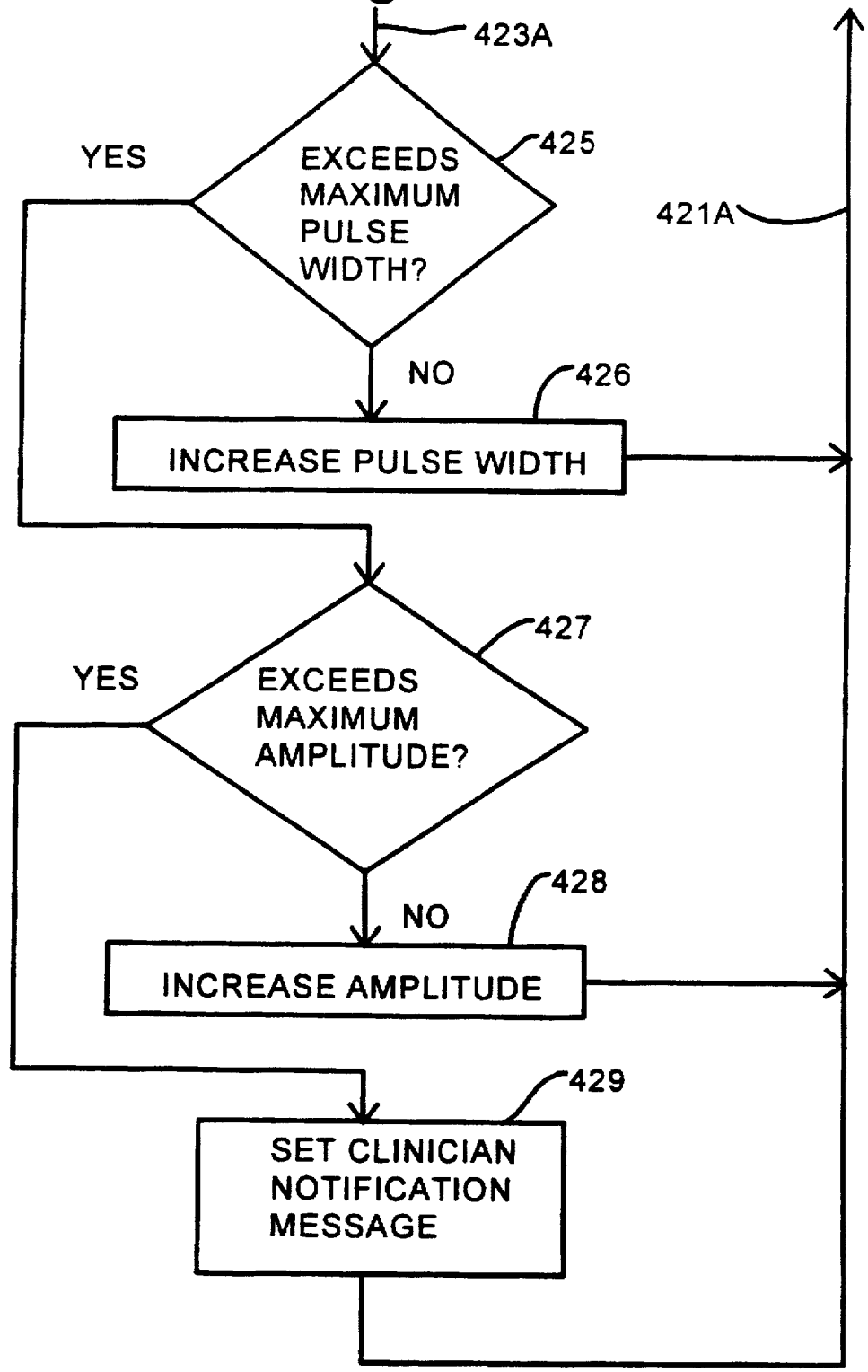
Figure 6:
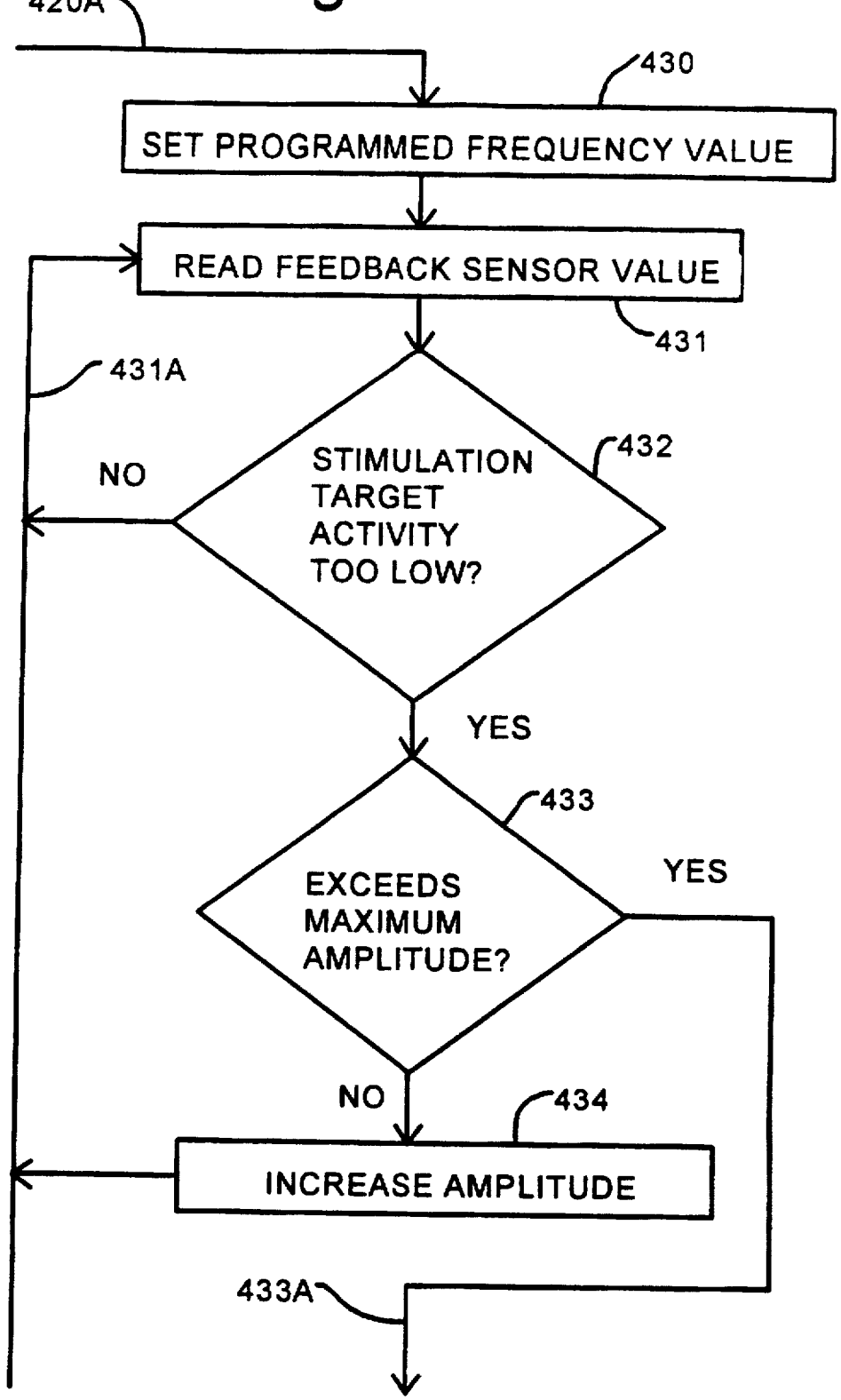

The algorithm uses the clinician programmed indication of whether the neurons at the particular location of the stimulating electrode are to be facilitated or blocked in order to reduce the neural activity in the subthalamic nucleus to decide which path of the parameter selection algorithm to follow (step 420, FIG. 4). If the neuronal activity is to be blocked, device 10 first reads the feedback sensor 130 in step 421. If the sensor values indicate the activity in the glutamatergic neurons is too high (step 422), the algorithm in this embodiment first increases the frequency of stimulation in step 424 provided this increase does not exceed the preset maximum value set by the physician. Step 423 checks for this condition. If the frequency parameter is not at the maximum, the algorithm returns to step 421 through path 421A to monitor the feed back signal from sensor 130. If the frequency parameter is at the maximum, the algorithm next increases the pulse width in step 426 (FIG. 5), again with the restriction that this parameter has not exceeded the maximum value as checked for in step 425 through path 423A. Not having reached maximum pulse width, the algorithm returns to step 421 to monitor the feedback signal from sensor 130. Should the maximum pulse width have been reached, the algorithm next increases amplitude in a like manner as shown in steps 427 and 428. In the event that all parameters reach the maximum, a notification message is set in step 429 to be sent by telemetry to the clinician indicating that device 10 is unable to reduce neural activity to the desired level.

Figure 7:
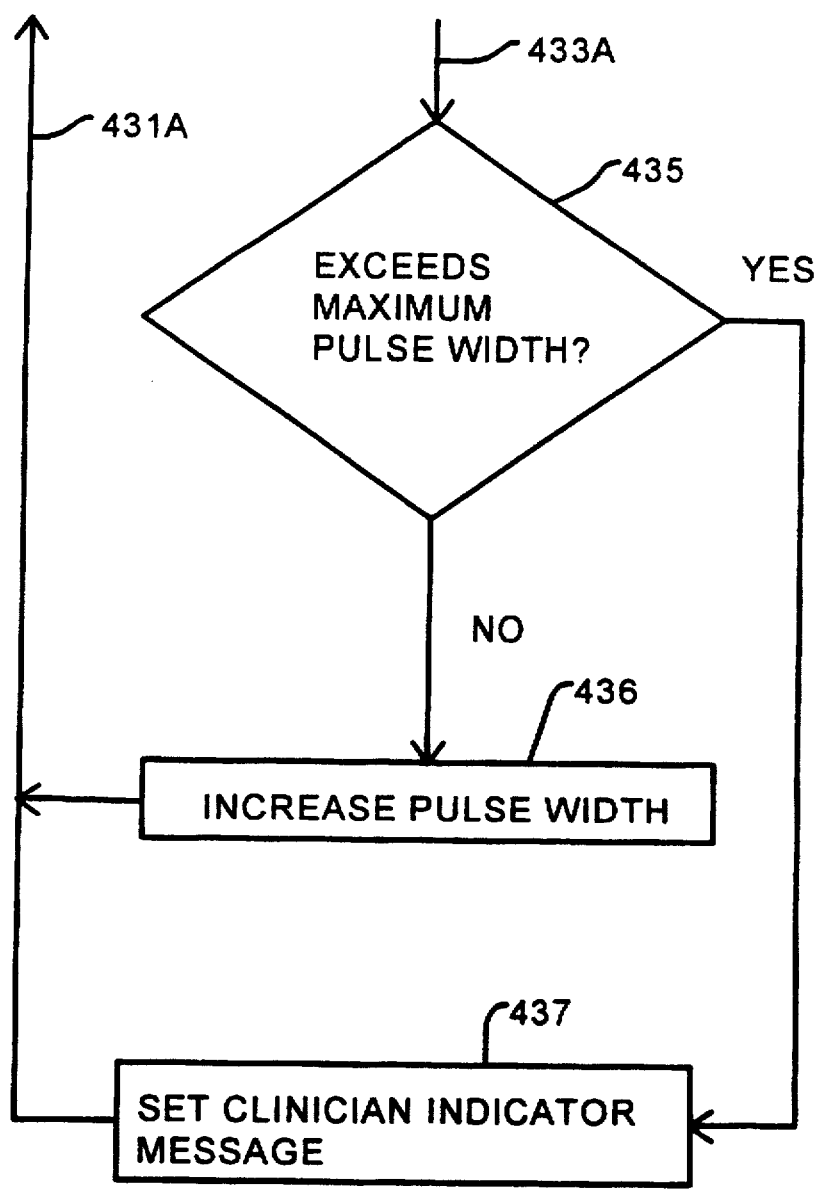

If, on the other hand, the stimulation electrode is placed in a location which the clinician would like to activate in order to increase an inhibition of the subthalamic nucleus, the algorithm would follow a different sequence of events. In the preferred embodiment, the frequency parameter would be fixed at a value chosen by the clinician to facilitate neuronal activity in step 430 (FIG. 6) through path 420A. In steps 431 and 432 the algorithm uses the values of the feedback sensor to determine if neuronal activity is being adequately controlled. In this case, inadequate control indicates that the neuronal activity of the stimulation target is too low. Neuronal activity is increased by first increasing stimulation amplitude (step 434) provided it doesn't exceed the programmed maximum value checked for in step 433. When maximum amplitude is reached, the algorithm increases pulse width to its maximum value in steps 435 and 436 (FIG. 7). A lack of adequate reduction of neuronal activity in the subthalamic nucleus, even though maximum parameters are used, is indicated to the clinician in step 437. After steps 434, 436 and 437, the algorithm returns to step 431 through path 431A, and the feedback sensor again is read.

It is desirable to reduce parameter values to the minimum level needed to establish the appropriate level of neuronal activity in the subthalamic nucleus. Superimposed on the algorithm just described is an additional algorithm to readjust all the parameter levels downward as far as possible. In FIG. 3, steps 410 through 415 constitute the method to do this. When parameters are changed, a timer is reset in step 415. If there is no need to change any stimulus parameters before the timer has counted out, then it may be possible due to changes in neuronal activity to reduce the parameter values and still maintain appropriate levels of neuronal activity in the target neurons. At the end of the programmed time interval, device 10 tries reducing a parameter in step 413 to determine if control is maintained. If it is, the various parameter values will be ratcheted down until such time as the sensor values again indicate a need to increase them. While the algorithms in FIG. 3 follow the order of parameter selection indicated, other sequences may be programmed by the clinician.

The present invention may be implemented by providing pulses to lead 22A having amplitudes of 0.1 to 20 volts, pulse widths varying from 0.02 to 1.5 milliseconds, and repetition rates varying from 2 to 2500 Hz. The appropriate stimulation pulses are generated by device 10 based on the computer algorithm shown in FIGS. 3–7 that read the output of converter 140 and makes the appropriate analysis.

The type of stimulation administered by device 10 to the brain depends on the specific location at which the electrodes 115 of lead 22A are surgically implanted. The appropriate stimulation for the portion of the basal ganglia or thalamus in which lead 22A terminates, together with the effect of the stimulation on that portion of the brain for neurodegenerative disorders, is provided in the following Table I:

TABLE I

| EFFECT | STIMULUS TYPE | LOCATION |
|---|---|---|
| INCREASE EXCITATION OF VL THALAMUS | LOW FREQ. STIMULATION | VL THALAMUS |
| DECREASE INHIBITION OF VL THALAMUS | HIGH FREQ. BLOCKING STIMULATION | GPi/SNr |
| INCREASE INHIBITION OF GPi/SNr | LOW FREQ. STIMULATION | STRIATOPALLIDAL FIBER |
| INCREASE INHIBITION OF GPi/SNr | LOW FREQ. STIMULATION | NEOSTRIATUM |
| DECREASE EXCITATION OF GPi/SNr | HIGH FREQ. BLOCKING STIMULATION | GPi/SNr |
| INCREASE INHIBITION OF STN | LOW FREQ. STIMULATION | GPe to STN FIBER PATHWAY |
| INCREASE INHIBITION OF STN | LOW FREQ. STIMULATION | GPe |
| INCREASE EXCITATION OF GPe | LOW FREQ. ACTIVATING STIMULATION | GPe |

TABLE I-continued

| EFFECT | STIMULUS TYPE | LOCATION |
|---|---|---|
| DECREASE INHIBITION OF GPe | HIGH FREQ BLOCKING STIMULATION | NEOSTRIATUM |

In the foregoing Table I, VL Thalamus means ventrolateral thalamus; GPi means internal segment of globus pallidus; SNr means substantia nigra pars reticulata, STN means subthalamic nucleus; and GPe means external segment of globus pallidus. High frequency stimulation is provided by electrical pulses having a repetition rate in the range of 50 to 2500 Hz. Low frequency stimulation is provided by electrical pulses having a repetition rate in the range of 2 to 100 Hz.

Typical stereotaxic coordinates for the portions of a normal brain described in Table I are identified in the following Table II:

TABLE II

| BRAIN REGION | MEDIAL-LATERAL DIMENSION | DORSAL-VENTRAL DIMENSION | ANTERIOR-POSTERIOR DIMENSION |
|---|---|---|---|
| VL Thalamus | 0.7 to 1.8 | 1.5 to –0.2 | 0.0 to –1.0 |
| GPi | 0.5 to 2.0 | 0.5 to –0.7 | 0.7 to 2.0 |
| SNr | 0.5 to 1.5 | –0.6 to –1.5 | 0.7 to –0.7 |
| STN | 0.5 to 2.0 | 0.0 to –1.0 | 0.6 to –1.0 |
| GPe | 1.6 to 2.7 | 1.0 to –1.0 | 2.0 to –1.0 |
| Neostriatum: | | | |
| Caudate | 0.5 to 2.0 | 1.5 to 3.0 | 1.5 to 3.0 |
| Putamen | 1.2 to 3.3 | 1.5 to –1.0 | 2.5 to –1.2 |

In the foregoing table: the medial-lateral dimensions are relative to midline of the brain; the anterior-posterior dimensions are relative to the midpoint between the anterior commissure and posterior commissure with negative indicating the posterior direction; the dorsal-ventral dimensions are relative to a line connecting the midpoints of the anterior and posterior commissures with negative being ventral to the line; all dimension are in centimeters.

Microprocessor 200 within device 10 can be programmed so that the desired stimulation can be delivered to the specific brain sites described in Table II. Alternatively, sensor 24 can be used with a closed loop feedback system in order to automatically determine the type of stimulation necessary to reduce the effect of neurodegenerative disorders as described in connection with FIGS. 3–7.

By using the foregoing techniques, the effects of neurodegenerative disorders can be controlled with a degree of accuracy previously unattainable.

Those skilled in the art will recognize that the preferred embodiments may be altered or amended without departing from the true spirit and scope of the invention, as defined in the accompanying claims.

I claim:

1. A system for treating a neurodegenerative disorder characterized by hyperexcitation of a portion of a brain comprising in combination:

an implantable signal generator for providing stimulation pulses;

an implantable electrode having a proximal end coupled to said signal generator and a stimulation portion adapted to stimulate a predetermined site in a brain;

a sensor for transmitting a signal related to the excitation of the portion of the brain exhibiting hyperexcitation; and a microprocessor responsive to said sensor signal for regulating at least one parameter of said stimulation by said implantable electrode, said at least one parameter being selected from the group consisting of pulse width, pulse frequency, and pulse amplitude.

2. A system, as claimed in claim 1, wherein said sensor comprises a sensor of electrical activity.

3. A system, as claimed in claim 1, wherein said sensor comprises an electrochemical sensor.

4. A system, as claimed in claim 3, wherein said electrochemical sensor is responsive to the amount of glutamate present in the substantia nigra.

5. A method of treating a neurodegenerative disorder characterized by hyperexcitation comprising in combination:

implanting a signal generator in a body of a patient;

implanting at least one electrode to be in communication with at least one predetermined site in the brain of said body;

coupling said at least one electrode to said signal generator;

pulse stimulating said at least one predetermined site in said brain of said body using said at least one electrode;

implanting a sensor in said body for generating a sensor signal related to the extent of hyperexcitation exhibited by a portion of said brain; and regulating at least one parameter of said step of stimulating in response to said sensor signal, said at least one parameter being selected from the group consisting of pulse width, pulse frequency, and pulse amplitude.

6. A method, as claimed in claim 5, wherein said neurodegenerative disorder is Parkinson's disease and wherein said step of stimulating is performed to increase thalamic output.

7. A method, as claimed in claim 6, wherein said step of stimulating increases excitement of the thalamus or decreases inhibition of the thalamus.

8. A method, as claimed in claim 7, wherein said step of stimulating increases inhibition or decreases excitation of an internal segment of globus pallidus (GPi) or substantia nigra pars reticulata (SNr).

9. A method, as claimed in claim 7, wherein said step of stimulating increases excitation or decreases inhibition of an external segment of globus pallidus (Gpe).

10. A method, as claimed in claim 5, wherein said signal generator operates in a high frequency range of 50 to 2500 Hz and said at least one predetermined site in said brain of said body is selected from the group consisting of the internal segment of globus pallidus (Gpi), substantia nigra pars reticulata (SNr) and the neostriatum.

11. A method, as claimed in claim 5, wherein said signal generator operates in a low frequency range of 2 to 100 Hz and said at least one predetermined site in said brain of said body is selected from the group consisting of the ventrolateral thalamus (Thal), striatopallidal fiber pathway, neostriatum, external segment of globus pallidus (Gpe), and external segment of globus pallidus to subthalamic nucleus fiber pathway.

12. A method of treating a neurodegenerative disorder characterized by hyperexcitation comprising in combination:

implanting at least one electrode to be in communication with at least one predetermined site in the brain of said body;

coupling said at least one electrode to a signal generator;

pulse stimulating said at least one predetermined site in said brain of said body using said at least one electrode;

generating a sensor signal related to the extent of hyperexcitation exhibited by a portion of said brain; and regulating at least one parameter of said step of stimulating in response to said sensor signal, said at least one parameter being selected from the group consisting of pulse width, pulse frequency, and pulse amplitude.

13. A method, as claimed in claim 12, wherein said neurodegenerative disorder is Parkinson's disease and wherein said step of stimulating is performed to increase thalamic output.

14. A method, as claimed in claim 13, wherein said step of stimulating increases excitement of the thalamus or decreases inhibition of the thalamus.

15. A method, as claimed in claim 14, wherein said step of stimulating increases inhibition or decreases excitation of said internal segment of globus pallidus (GPi) or substantia nigra pars reticulata (SNr).

16. A method, as claimed in claim 14, wherein said step of stimulating increases excitation or decreases inhibition of said external segment of globus pallidus (Gpe).

17. A method, as claimed in claim 12, wherein said signal generator operates in a high frequency range of 50 to 2500 Hz and said at least one predetermined site in said brain of said body is selected from the group consisting of the internal segment of globus pallidus (Gpi), substantia nigra pars reticulata (SNr) and the neostriatum.

18. A method, as claimed in claim 12, wherein said signal generator operates in a low frequency range of 2 to 100 Hz and said at least one predetermined site in said brain of said body is selected from the group consisting of the ventrolateral thalamus (Thal), striatopallidal fiber pathway, neostriatum, external segment of globus pallidus (Gpe), and external segment of globus pallidus to subthalamic nucleus fiber pathway.

* * * * *